(12) United States Patent
Yamazaki et al.

(10) Patent No.: US 11,001,713 B2
(45) Date of Patent: *May 11, 2021

(54) ORGANIC/INORGANIC COMPOSITE FILLER AND MANUFACTURING METHOD THEREFOR

(71) Applicant: TOKUYAMA DENTAL CORPORATION, Tokyo (JP)

(72) Inventors: Tatsuya Yamazaki, Tokyo (JP); Hironobu Akizumi, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 130 days.

This patent is subject to a terminal disclaimer.

(21) Appl. No.: 15/991,687

(22) Filed: May 29, 2018

(65) Prior Publication Data

US 2018/0273766 A1 Sep. 27, 2018

Related U.S. Application Data

(63) Continuation of application No. 13/583,687, filed as application No. PCT/JP2011/055757 on Mar. 11, 2011, now Pat. No. 10,005,910.

(30) Foreign Application Priority Data

Mar. 19, 2010 (JP) .............................. JP2010-063979
Jan. 13, 2011 (JP) .............................. JP2011-005207

(51) Int. Cl.
*C09C 3/10* (2006.01)
*C09C 1/30* (2006.01)
(Continued)

(52) U.S. Cl.
CPC .................. *C09C 3/10* (2013.01); *A61K 6/71* (2020.01); *A61K 6/836* (2020.01); *A61K 6/887* (2020.01);
(Continued)

(58) Field of Classification Search
CPC ....... C09C 3/10; C09C 1/2072; C09C 1/3676; A61K 6/887; A61K 6/71; B82Y 30/00;
(Continued)

(56) References Cited

U.S. PATENT DOCUMENTS 4,764,497 A 8/1988 Yuasa et al.
6,221,931 B1 4/2001 Sakuma et al.
(Continued)

FOREIGN PATENT DOCUMENTS

EP 1149573 A2 10/2001
JP 58-110414 A 7/1983
(Continued)

OTHER PUBLICATIONS

Machine translation of JP 2007-314484 by Kaneyasu et al. (Year: 2007).*

(Continued)

*Primary Examiner* — Michael M Dollinger
*Assistant Examiner* — Christina H. W. Rosebach
(74) *Attorney, Agent, or Firm* — Norris McLaughlin, P.A.

(57) ABSTRACT

Disclosed is an organic/inorganic composite filler that contains: inorganic agglomerated particles comprising agglomerations of inorganic primary particles having a mean diameter between 10 and 1000 nm; an organic resin phase that covers the surface of each inorganic primary particle and binds the inorganic primary particles to each other; and intra-agglomerate voids, formed between the organic resin phase covering the surface of each inorganic primary particle, with a pore volume (here, "pore" refers to holes with diameters between 1 and 500 nm) between 0.01 and 0.30 $cm^3/g$ as measured by mercury intrusion porosimetry. Also disclosed is a method for manufacturing the above organic/inorganic composite filler.

4 Claims, 1 Drawing Sheet

(51) Int. Cl.

| | | |
|---|---|---|
| C09C 1/36 | (2006.01) | |
| B82Y 30/00 | (2011.01) | |
| A61K 6/71 | (2020.01) | |
| A61K 6/836 | (2020.01) | |
| A61K 6/887 | (2020.01) | |
| C08L 33/06 | (2006.01) | |

(52) U.S. Cl.
CPC ............... B82Y 30/00 (2013.01); C08L 33/06 (2013.01); C09C 1/3072 (2013.01); C09C 1/3676 (2013.01); *C01P 2002/50* (2013.01); *C01P 2004/32* (2013.01); *C01P 2004/64* (2013.01); *C01P 2006/14* (2013.01)

(58) Field of Classification Search
CPC .. C08L 33/06; C01P 2002/50; C01P 2004/32; C01P 2004/64; C01P 2006/14
See application file for complete search history.

(56) References Cited

U.S. PATENT DOCUMENTS

| 2002/0022677 A1 | 2/2002 | Teramae et al. |
| 2013/0005846 A1 | 1/2013 | Yamazaki et al. |

FOREIGN PATENT DOCUMENTS

| JP | 58-151321 A | 9/1983 |
| JP | 58-156524 A | 9/1983 |
| JP | 58-156526 A | 9/1983 |
| JP | 2000-80013 A | 3/2000 |
| JP | 2001-302429 A | 10/2001 |
| JP | 2003012460 A | 1/2003 |
| JP | 2006-89378 A | 4/2006 |
| JP | 2007-314484 A | 12/2007 |
| JP | 2007314484 A | 12/2007 |
| JP | 2008-37952 A | 2/2008 |

OTHER PUBLICATIONS

M. Barari; N. Sharifi-Sanjani. "Synthesis of Poly(methyl methacrylate)/Silica Nanocomposite Through Emulsion Polymerization Using Dimethylaminoethyl Methacrylate". Journal of Applied Polymer Science, vol. 110, 929-937 (2008) (Year: 2008).*

Guangwei Jia, Zhiqiang Cao, Hong Xue, Yongshen Xu, and Shaoyi Jiang. Novel Zwitterionic-Polymer-Coated Silica Nanoparticles. Langmuir 2009, 25, 3196-3199. (Year: 2009).*

International Search Report for corresponding application PCT/JP2011/055757 dated Mar. 30, 2011.

Jia, G., et al., "Novel Zwitterionic-Polymer-Coated Silica Nanoparticles", Langmuir, 2009, pp. 3196-3199.

Suffner, J.; , et al. "In-situ Coating of Silica Nanoparticles with Acrylate-Based Polymers", Chemical Vapor Deposition, 2007, pp. 459-464.

Barari, M., et al. "Synthesis of Poly(methyl methacrylate)/Silica Nanocomposite Through Emulsion Polymerization Using Dimethylaminoethyl Methacrylate", J. App. Poly Sci., 2008, pp. 929-937.

Itoh, Y.; "Preparation of Biodegradable Hollow Nanocapsules by Silica Template Method", Chem Lett, vol. 33 pp. 1552-1553, 2004.

* cited by examiner

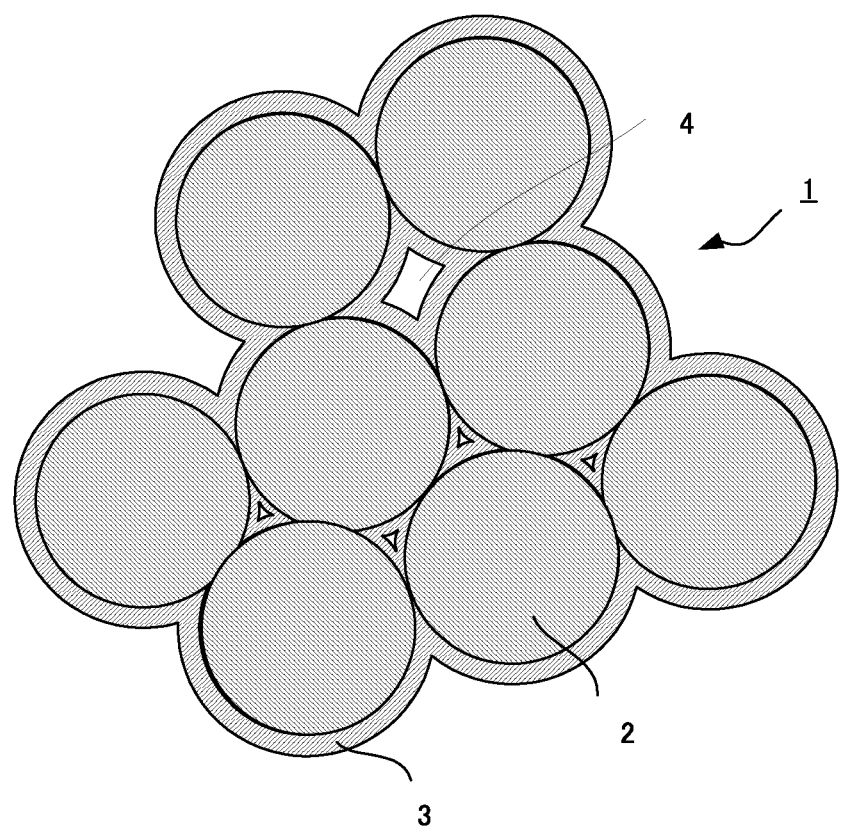

ORGANIC/INORGANIC COMPOSITE FILLER AND MANUFACTURING METHOD THEREFOR

This application is a continuation of U.S. application Ser. No. 13/583,687, filed Sep. 10, 2012, which is a § 371 U.S. National stage of PCT International Patent Application No. PCT/JP2011/055757, filed Mar. 11, 2011, which claims foreign priority benefit of Japanese Patent Application No. 2011-005207, filed Jan. 13, 2011, and Japanese Patent Application No. 2010-063979, filed Mar. 19, 2010, the disclosures of each of which patent applications are incorporated herein by reference.

TECHNICAL FIELD

The present invention relates to an organic-inorganic composite filler, a manufacturing method therefor, and a dental curable composition containing the organic-inorganic composite filler.

BACKGROUND ART

Dental composite restorative materials are typical dental curable compositions. In a dental clinic, for example, a dental composite restorative material is filled into the cavity of a tooth to be restored, formed into the tooth shape, and then polymerized and cured by irradiation with active light using a special irradiator, so that the damaged tooth is restored.

In a dental laboratory, a dental composite restorative material on a plaster cast is built in the form of a tooth to be restored and then polymerized and cured by light irradiation. In a dental clinic, the product is bonded to the tooth with a dental adhesive, so that the damaged tooth is restored.

Dental composite restorative materials are advantageous in that they can have substantially the same color as that of natural teeth and good handling property. In recent years, therefore, dental composite restorative materials have spread rapidly, and now they have been used in most of the front teeth treatments. Dental composite restorative materials with considerably high mechanical strength have also been developed. As a result, dental composite restorative materials are also beginning to be used in the restoration of posterior teeth, to which high bite pressure is applied.

A dental composite restorative material generally includes a polymerizable monomer (monomer), a filler, and a polymerization initiator as main components. The material, shape, particle size, and content of the filler to be used are selected, when a dental composite restorative material is formed. When they are selected appropriately, various properties such as the handling property of the dental composite restorative paste and the esthetics, mechanical strength, and other properties of the cured product are controlled optimally.

For example, when an inorganic filler with a large particle size is added to a dental composite restorative material, the resulting composite restorative material can form a cured product with high mechanical strength. This is advantageous to the dental composite restorative material. On the other hand, however, the cured product can have reduced surface smoothness or wear resistance. As a result, it may be difficult to obtain a cured product with a glossy finish surface like natural teeth.

A fine inorganic filler with an average particle size of 1 μm or less can also form a cured product with good surface smoothness or wear resistance. However, a fine inorganic filler, which has a large specific surface area, can significantly increase the viscosity of a paste composite restorative material. Meanwhile, in the treatment of teeth, it is necessary for a dentist to adjust the viscosity of a composite restorative material to a level suitable for use in the oral cavity. In order to reduce the viscosity, it is necessary to reduce the content of a fine inorganic filler. In this case, problems may occur, such as a reduction in handling property during treatment, an increase in the shrinkage of a cured product, which is associated with the polymerization of a monomer during the curing of a composite restorative material, and a reduction in the mechanical strength of the resulting cured material.

Under the circumstances, the use of an organic-inorganic composite filler is proposed (see for example Patent Literatures 1 and 2). According to these Patent Literatures, when such an organic-inorganic composite filler is used, a paste composite restorative material with good handling property can be obtained with good surface smoothness and wear resistance maintained as in the case where a fine inorganic filler is used, and the polymerization shrinkage of the cured product is also reduced.

Such an organic-inorganic composite filler includes an organic resin filler and a fine inorganic filler contained therein. The organic-inorganic composite filler has a surface area smaller than that of the fine inorganic filler. Therefore, a sufficient amount of the organic-inorganic composite filler can be added without causing thickening when a paste composite restorative material is manufactured.

A general method of manufacturing the organic-inorganic composite filler includes preliminarily kneading a fine inorganic filler and a polymerizable monomer to form a curable composition, polymerizing the curable composition to form a cured product, and then grinding the cured product (see paragraph [0012] of Patent Literature 1).

There is also known a method for manufacturing an organic-inorganic composite filler with a narrow particle size distribution (see Claims of Patent Literature 2). In this method, inorganic agglomerated particles are first manufactured by a method of granulating a fine inorganic filler, such as spray drying. Subsequently, the manufactured inorganic agglomerated particles, which are in contact with a liquid polymerizable monomer under reduced pressure, are allowed to return to the original pressure, so that the polymerizable monomer is allowed to penetrate the intra-agglomerate voids of primary particles constituting the inorganic agglomerated particles.

Subsequently, the penetrating monomer is polymerized and cured to form an organic-inorganic composite filler. This organic-inorganic composite filler may also be used without being ground.

The Literature states that in the manufacturing method, the polymerizable monomer may be diluted with a volatile solvent when the inorganic agglomerated particles are brought into contact with the polymerizable monomer (paragraphs [0042]-[0043]). The reason is that the polymerizable monomer should be allowed to sufficiently penetrate the intra-agglomerate voids of the inorganic agglomerated particles.

Unfortunately, the description of the Literature is silent on how much the volatile solvent should be used and particularly silent on what process should be used to remove the volatile solvent after the monomer is allowed to penetrate the intra-agglomerate voids. The Literature also discloses dropping or continuous mixing as a method for bringing the polymerizable monomer into contact with the inorganic agglomerated particles, in which such a continuous operation allows as much the polymerizable monomer as possible to penetrate the intra-agglomerate voids of the inorganic agglomerated particles.

From the description of the Literature, therefore, it is apparent that even the mode of diluting the polymerizable monomer with a volatile solvent is no different from the technical idea of charging the polymerizable monomer as much as possible into the intra-agglomerate voids. In other words, it suggests that the volatile solvent should be used in a minimum amount. Therefore, it is considered that in the mode of diluting the polymerizable monomer with a volatile solvent, the dilute solution of the polymerizable monomer is allowed to penetrate the intra-agglomerate voids, while the volatile solvent is evaporated from the penetrating dilute solution. Thus, it is considered that the dilution mode is intended to charge a sufficient amount of the polymerizable monomer into the whole of the intra-agglomerate voids based on the continuation of the penetration and the evaporation before the polymerization and curing.

CITATION LIST

Patent Literature

Patent Literature 1: Japanese Patent Application Laid-Open (JP-A) No. 2000-80013
Patent Literature 2: JP-A No. 2008-37952

SUMMARY OF INVENTION

Technical Problem

Dental composite restorative materials containing an organic-inorganic composite filler, which are obtained by the conventional technique have considerably high mechanical strength. Unfortunately, as such materials are used to restore posterior teeth, on which high bite pressure is loaded as mentioned above, there has been an increasing demand for the improvement of the mechanical strength of organic-inorganic composite fillers. Thus, it is desired to further increase the mechanical strength of organic-inorganic composite fillers.

Under the circumstances, an object of the present invention is to develop an organic-inorganic composite filler that can form a cured product with further increased mechanical strength, when added to a dental curable composition.

Solution to Problem

The inventors have made earnest studies to solve the above problems. As a result, the inventors have accomplished the present invention based on the finding that the above problems can be solved when the intra-agglomerate voids of inorganic primary particles in an organic-inorganic composite filler are not completely filled with the organic resin phase so that voids having a specific pore volume are left in the organic-inorganic composite filler.

Thus, the present invention is directed to an organic-inorganic composite filler, comprising:

inorganic agglomerated particles including agglomerates of inorganic primary particles with an average particle size of 10 to 1,000 nm;

an organic resin phase with which the surface of each inorganic primary particle is coated and with which the inorganic primary particles are bonded together; and intra-agglomerate voids that are formed between parts of the organic resin phase, with which the surface of each inorganic primary particle is coated, and has a pore volume of 0.01 to 0.30 $cm^3/g$ as measured by mercury intrusion porosimetry, wherein the pore volume corresponds to the volume of pores with pore sizes in the range of 1 to 500 nm.

The present invention also provides a method of suitably manufacturing the organic-inorganic composite filler in which intra-agglomerate voids of inorganic primary particles are formed having the above pore volume, which comprises the steps of:

immersing inorganic agglomerated particles, which include agglomerates of inorganic primary particles with an average particle size of 10 to 1,000 nm, in a polymerizable monomer solution containing 100 parts by mass of an organic solvent, 3 to 70 parts by mass of a polymerizable monomer, and an effective amount of a polymerization initiator;

removing the organic solvent from the inorganic agglomerated particles after the immersion;

polymerizing and curing the polymerizable monomer with which the inorganic agglomerated particles are impregnated.

Advantageous Effects of Invention

The organic-inorganic composite filler of the present invention can effectively form a dental curable composition that not only has good paste handling property and a reduced amount of polymerization shrinkage, but also forms a cured product with significantly improved surface smoothness, wear resistance, and mechanical strength. These effects are produced when pores formed by intra-agglomerate voids of inorganic primary particles have a specific pore volume in the organic-inorganic composite filler. Specifically, it is considered that a polymerizable monomer in a curable composition can penetrate by capillarity through such pores formed by intra-agglomerate voids, so that an anchoring effect can be produced by curing the monomer, which enables the organic-inorganic composite filler to be retained with high interlocking strength in the curing product of the curable composition, so that the mechanical strength is improved.

The organic-inorganic composite filler of the present invention having such an advantageous effect can be used, without limitation, in a variety of applications such as dental materials and cosmetic materials. Specifically, dental materials include dental curable compositions such as dental restorative filling materials such as composite resins; indirect dental restorative materials for inlay, onlay, crown, and bridge; dental cement; and denture materials. In particular, the organic-inorganic composite filler is suitable for use as a filler to be added to dental composite restorative materials such as dental restorative filling materials and indirect dental restorative materials.

BRIEF DESCRIPTION OF DRAWING

FIG. 1 is a schematic cross-sectional view showing a typical mode of the organic-inorganic composite filler of the present invention.

REFERENCE SIGNS LIST

1: Organic-inorganic composite filler
2: Inorganic primary particles
3: Organic resin phase
4: Intra-agglomerate voids

DESCRIPTION OF EMBODIMENTS (Organic-Inorganic Composite Filler)

The organic-inorganic composite filler of the present invention includes agglomerates of inorganic primary particles with an average particle size of 10 to 1,000 nm, in which the surface of each inorganic primary particle is coated with an organic resin phase, and the inorganic primary particles are bonded together with the organic resin phase. The spaces between the inorganic primary particles are not completely filled with the organic resin phase. Pores of intra-agglomerate voids are formed between parts of the organic resin layer with which the surfaces of a large number of inorganic primary particles are coated. Specifically, in the intra-agglomerate voids of the inorganic primary particles coated with the organic resin phase, pores with pore sizes in the range of 1 to 500 nm are formed having a volume of 0.01 to 0.30 cm$^3$/g as measured by mercury intrusion porosimetry. As described above, a polymerizable monomer contained in a curable composition penetrates the intra-agglomerate voids by capillarity. As a result, the cured resin, which is manufactured by curing the polymerizable monomer, is embedded in the pores and strongly bonded to the organic-inorganic composite filler. Therefore, the curable composition containing the organic-inorganic composite filler of the present invention can form a cured product with high mechanical strength by deriving a so-called anchoring effect with the aid of pores.

Such a characteristic pore structure of the organic-inorganic composite filler of the present invention is described using FIG. 1, which is a schematic diagram illustrating a particle cross-section. The organic-inorganic composite filler 1 has agglomerates of a plurality of inorganic primary particles 2 with an average particle size of 10 to 1,000 nm. The surfaces of the plurality of inorganic primary particles 2 are each coated with an organic resin phase 3, and the organic resin phases 3 are melted together and integrally solidified so that they are strongly bonded together.

The spaces formed by agglomerates of the plurality of inorganic primary particles are not completely filled with the organic resin phase 3, so that intra-agglomerate voids 4 are left. Among all pores formed by the intra-agglomerate voids 4, the total volume of pores with pore sizes in the range of 1 to 500 nm is from 0.01 to 0.30 cm$^3$/g, preferably from 0.03 to 0.20 cm$^3$/g as measured by the mercury intrusion porosimetry described below.

In the present invention, the pore volume of the organic-inorganic composite filler is a value measured by mercury intrusion porosimetry. The pore volume can be measured by mercury intrusion porosimetry as described below.

First, a predetermined amount of the organic-inorganic composite filer is placed in a measurement cell. Subsequently, the amount of injected mercury is measured using a mercury porosimeter at a pressure corresponding to each diameter of pores formed in the intra-agglomerate voids of the organic-inorganic composite filler. The pore volume is then calculated by summing the amounts of injected mercury for the respective pores. As stated above, the diameters of the pores to be measured for the pore volume are in the range of 1 to 500 nm.

There may be considered weak agglomerates of inorganic primary particles, hollow agglomerates of inorganic primary particles, etc. An organic-inorganic composite filler manufactured using such agglomerates may have large pores with pore sizes of more than 500 nm. Sufficient capillarity may hardly occur in such pores with large pore sizes. In this case, a polymerizable monomer contained in a curable composition cannot sufficiently penetrate the pores, so that an anchoring effect may fail to be produced sufficiently. Otherwise, when the pores are huge, some voids are left even though a polymerizable monomer is charged into the inside, so that the anchoring effect may hardly occur sufficiently.

In the present invention, the presence of such large pores in the organic-inorganic composite filler is acceptable. However, huge pores are not counted as the pores to be measured when the pore volume is determined. On the other hand, it is difficult for mercury intrusion porosimetry to determine the volume of pores with pore sizes of less than 1 nm. In addition, as the organic resin phase is formed, pores with small pore sizes become closed. It is therefore considered that such pores are difficult to remain, and even if such pores exist, the anchoring effect will not occur sufficiently in such pores. In the present invention, therefore, pores with pore sizes out of the above pore size range are not counted as the pores to be measured for the pore volume.

If an organic-inorganic composite filler in which the pore volume is less than 0.01 cm$^3$/g is added to a curable composition, only a small amount of a polymerizable monomer can penetrate the pores. As a result, a sufficient anchoring effect cannot be produced, so that the resulting cured product may have low mechanical strength.

If the pore volume is more than 0.30 cm$^3$/g, the organic-inorganic composite filler itself may become brittle, and the filler may also be difficult to manufacture. Therefore, in order to produce these effects at a higher level, the pore volume of the organic-inorganic composite filler is particularly preferably from 0.03 to 0.20 cm$^3$/g.

The average pore size of the pores formed by the intra-agglomerate voids of the organic-inorganic composite filler is preferably, but not limited to, 3 to 300 nm, more preferably 10 to 200 nm. When the average pore size is in the above range, intra-agglomerate voids having the above pore volume can be formed easily. The average pore size of the pores formed by the intra-agglomerate voids refers to a median pore diameter, which is determined on the basis of the pore volume distribution of the pores with pore sizes in the range of 1 to 500 nm as measured by mercury intrusion porosimetry.

The average particle size (grain size) of the organic-inorganic composite filler is preferably from 3 to 100 μm, in particular, preferably from 5 to 70 μm. If the average particle size is less than 3 μm, a dental curable composition can be filled with the filler at a low filling rate. As a result, the cured product has low mechanical strength, or the dental curable composition has high viscosity, so that the handling property during dental treatment may be degraded. If the average particle size is more than 100 μm, the dental curable composition has low fluidity. As a result, the handling property during dental treatment is degraded.

The average particle size of the organic-inorganic composite filler refers to a median diameter, which is determined on the basis of a particle size distribution obtained by laser diffraction-scattering method. The sample to be subjected to the measurement is prepared by uniformly dispersing 0.1 g of the organic-inorganic composite filler in 10 ml of ethanol.

The average particle size of the inorganic primary particles is from 10 to 1,000 nm, preferably from 40 to 800 nm, more preferably from 50 to 600 nm. If the inorganic primary particles have an average particle size of less than 10 nm, it may be difficult to form pores with the pore volume being characteristic of the present invention. In addition, the openings of the pores may be more likely to be blocked by the organic resin phase in the process of manufacturing the organic-inorganic composite filler. Therefore, the resulting filler may be more likely to have air bubble inclusions. If the organic-inorganic composite filler has air bubble inclusions, the cured product of a curable composition containing the organic-inorganic composite filler will have low transparency.

On one hand, if inorganic primary particles with an average particle size of more than 1,000 nm are used to form a dental composite restorative material or the like, the resulting cured product may have low polishability, which makes it difficult to obtain a cured product with a smooth surface.

The shape of the inorganic primary particles is not particularly restricted, and spherical, near-spherical, or irregular form particles may be used. The organic-inorganic composite filler should provide high wear resistance and surface smoothness and have uniform pores, and should be less likely to have air bubble inclusions, which are caused by the blocking of the openings of the pores by the organic resin phase. From these points of view, the inorganic primary particles are preferably spherical or near-spherical. The term "near-spherical" means that the average degree of symmetry is 0.6 or more. The average degree of symmetry is more preferably 0.7 or more, in particular, preferably 0.8 or more.

In the present invention, the primary particle size of the inorganic particles can be measured using a scanning or transmission electron microscope. Specifically, the image of the organic-inorganic composite filler is subjected to image analysis, which determines the circle equivalent diameter of each inorganic primary particle (the diameter of a circle having the same area as the object particle). The electron microscopy image to be used should have a sharp contrast so that the contour of each particle can be identified.

The image analysis should be performed using image analysis software that enables at least the measurement of particle area, maximum particle length, and minimum width. Randomly selected 100 inorganic primary particles are measured for primary particle size (circle equivalent diameter), maximum particle length, and minimum width by the above method, and the average particle size and the average degree of symmetry of the inorganic primary particles are calculated from the formulae below.

$$\text{Average particle size: } X = \sqrt[3]{\frac{\sum_{i=1}^{n} X_i^3}{n}} \text{ (average volume diameter)} \quad \text{[Formula 1]}$$

n: the number of observed particles
Xi: the particle size (diameter) of the i-th particle $$\text{Average degree of symmetry} = \frac{\sum_{i=1}^{n} Bi/Li}{n} \quad \text{[Formula 2]}$$

In the formulae, (n) is defined as the number of particles, the long diameter ($L_i$) is defined as the maximum length of the i-th particle, and the minimum width ($B_i$) is defined as the diameter in the direction perpendicular to the long diameter.

The inorganic primary particles may be made of any material used to use a filler for conventional dental curable compositions. Examples of such a material include an elemental metal selected from the group consisting of metals of Groups I, II, III and IV, transition metals or the like of the periodic table; oxides or complex oxides of these metals; salts of these metals, such as fluorides, carbonates, sulfates, silicates, hydroxides, chlorides, sulfites, and phosphates of these metals; and composites of these salts of metals. Preferably used are metal oxides such as amorphous silica, quartz, alumina, titania, zirconia, barium oxide, yttrium oxide, lanthanum oxide, and ytterbium oxide; silica-based complex oxides such as silica-zirconia, silica-titania, silica-titania-barium oxide, and silica-titania-zirconia; glass such as borosilicate glass, aluminosilicate glass, or fluoroaluminosilicate glass; metal fluorides such as barium fluoride, strontium fluoride, yttrium fluoride, lanthanum fluoride, and ytterbium fluoride; inorganic carbonates such as calcium carbonate, magnesium carbonate, strontium carbonate, and barium carbonate; and metal sulfates such as magnesium sulfate and barium sulfate.

Among these materials, metal oxides and silica-based complex oxides are preferably fired at high temperature so that dense materials can be obtained. To increase the firing effect, a small amount of an oxide of a metal of Group I of the periodic table, such as sodium, is preferably added to metal oxide and silica-based complex oxide.

Among inorganic primary particles of the above materials, silica-based complex oxide particles have refractive indices capable of being controlled easily. These particles are also particularly preferred, because they have a large amount of silanol groups on their surfaces, so that their surfaces can be easily modified using a silane coupling agent or the like.

Particles of silica-zirconia, silica-titania, silica-titania-barium oxide, or silica-titania-zirconia listed above are preferred because they have strong X-ray imaging properties. In addition, silica-zirconia particles are most preferred, because they can form a cured product with higher wear resistance.

These inorganic primary particles may be those manufactured by any known method. For example, inorganic oxide primary particles, complex oxide primary particles, or the like may be manufactured by any of a wet method, a dry method, and a sol-gel method. The inorganic primary particles are preferably manufactured by a sol-gel method, considering that the sol-gel method is advantageous in industrially manufacturing particles with a spherical shape and high monodispersity and can easily control the refractive index and easily impart X-ray imaging properties.

There are known methods for manufacturing spherical particles of silica-based complex oxide by sol-gel method, such as those disclosed in JP-A Nos. 58-110414, 58-151321, 58-156524, and 58-156526.

In these methods, a mixed solution containing a hydrolyzable organosilicon compound and optionally a hydrolyzable organic compound of another metal is first prepared. Subsequently, the mixed solution is added to an alkaline solvent, in which these organic compounds are soluble but the inorganic oxide to be manufactured is substantially insoluble, and subjected to hydrolysis. The hydrolysis results in the precipitation of an inorganic oxide. Therefore, the precipitate is separated by filtration and dried.

After the drying, the inorganic primary particles obtained in this manner may be fired at a temperature of 500 to 1,000° C. so that surface stability can be provided. During firing, part of the inorganic primary particles may agglomerate. In such a case, it is preferred that agglomerate particles are dissociated into primary particles by using a jet mill, a vibratory ball mill, or the like, and the particle size is adjusted within the predetermined range, before use. Such a process can increase the polishability and other properties of the product to be used as a dental composite restorative material.

The inorganic primary particles may be a mixture of two or more types of inorganic primary particles different in average particle size, material, or shape.

The organic resin phase, with which the surfaces of the inorganic primary particles are coated, may be formed using any known organic resin. Taking into account the preferred method described below for manufacturing the organic-inorganic composite filler, the organic resin is preferably a polymer of a polymerizable monomer. The polymerizable monomer is preferably compatible with organic solvents.

For example, the polymerizable monomer used to form the organic resin may be each of the monomers shown in sections A to D below.

A. Monofunctional Vinyl Monomer

Examples of monofunctional vinyl monomer include methacrylates such as methyl methacrylate, ethyl methacrylate, isopropyl methacrylate, hydroxyethyl methacrylate, tetrahydrofurfuryl methacrylate, and glycidyl methacrylate, and acrylates corresponding to the above; acrylic acid, methacrylic acid, p-methacryloyloxybenzoic acid, N-2-hydroxy-3-methacryloyloxypropyl-N-phenylglycine, 4-methacryloyloxyethyltrimellitic acid, and anhydrides thereof, 6-methacryloyloxyhexamethylenemalonic acid, 10-methacryloyloxydecamethylenemalonic acid, 2-methacryloyloxyethyldihydrogenphosphate, 10-methacryloyloxydecamethylenedihydrogenphosphate, and 2-hydroxyethylhydrogenphenylphosphonate.

B. Bifunctional Vinyl Monomer

B-1 Aromatic Compound Monomer

Examples of aromatic compound monomer include 2,2-bis(methacryloyloxyphenyl)propane, 2,2-bis[4-(3-methacryloyloxy)-2-hydroxypropoxyphenyl]propane, 2,2-bis(4-methacryloyloxyphenyl)propane, 2,2-bis(4-methacryloyloxypolyethoxyphenyl)propane, 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2-(4-methacryloyloxydiethoxyphenyl)-2-(4-methacryloyloxydiethoxyphenyl)propane, 2-(4-methacryloyloxydiethoxyphenyl)-2-(4-methacryloyloxyditriethoxyphenyl)propane, 2-(4-methacryloyloxydipropoxyphenyl)-2-(4-methacryloyloxytriethoxyphenyl)propane, 2,2-bis(4-methacryloyloxypropoxyphenyl)propane, 2,2-bis(4-methacryloyloxyisopropoxyphenyl)propane, and acrylates corresponding to these methacrylates; and diadducts obtained by the addition reaction between an OH group-containing vinyl monomer such as a methacrylate such as 2-hydroxyethyl methacrylate, 2-hydroxypropyl methacrylate, or 3-chloro-2-hydroxypropyl methacrylate, or an acrylate corresponding thereto and an aromatic group-containing diisocyanate compound such as diisocyanatomethyl benzene or 4,4'-diphenylmethane diisocyanate or the like.

B-2 Aliphatic Compound Monomer

Examples of aliphatic compound monomer include ethylene glycol dimethacrylate, diethylene glycol dimethacrylate, triethylene glycol dimethacrylate, butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate, and acrylates corresponding to these methacrylates; diadducts obtained by the addition reaction between an OH group-containing vinyl monomer such as a methacrylate such as 2-hydroxyethyl methacrylate, 2-hydroxypropyl methacrylate, or 3-chloro-2-hydroxypropyl methacrylate, or an acrylate corresponding thereto and a diisocyanate compound such as hexamethylene diisocyanate, trimethylhexamethylene diisocyanate, diisocyanatomethylcyclohexane, isophorone diisocyanate, or methylene bis(4-cyclohexylisocyanate); and acrylic anhydride, methacrylic anhydride, and 1,2-bis(3-methacryloyloxy-2-hydroxypropoxy)ethyl, di(2-methacryloyloxypropyl)phosphate or the like.

C Trifunctional Vinyl Monomer

Examples of trifunctional vinyl monomer include methacrylates such as trimethylolpropane trimethacrylate, trimethylolethane trimethacrylate, pentaerythritol trimethacrylate, trimethylolmethane trimethacrylate, and acrylates corresponding to these methacrylates or the like.

D Tetrafunctional Vinyl Monomer

Examples of tetrafunctional vinyl monomer include pentaerythritol tetramethacrylate, pentaerythritol tetraacrylate, and diadducts obtained by the addition reaction between glycidol dimethacrylate and a diisocyanate compound such as diisocyanatomethylbenzene, diisocyanatomethylcyclohexane, isophorone diisocyanate, hexamethylene diisocyanate, trimethylhexamethylene diisocyanate, methylenebis(4-cyclohexylisocyanate), 4,4-diphenylmethanediisocyanate, or tolylene-2,4-diisocyanate etc.

Among the above monomers, (meth)acrylic polymerizable monomers are preferred, because they can form polymers with high mechanical strength or biological safety. Bifunctional or polyfunctional polymerizable monomers are preferred, and bifunctional to tetrafunctional polymerizable monomers are more preferred, because they have high polymerizability or can form cured products with particularly high mechanical properties.

One of these polymerizable monomers may be used alone, or two or more different types of these polymerizable monomers may be used in combination.

When the organic-inorganic composite filler of the present invention is used as a filler for a dental curable composition, the polymerizable monomer is preferably so selected that there will be a difference of 0.1 or less between the refractive indices of the resulting polymer and the inorganic primary particles. When the monomer is selected in such a manner, sufficient transparency can be imparted to the resulting organic-inorganic composite filler. In addition, when the resulting organic-inorganic composite filler is used for a dental curable composition, the monomer is preferably so selected that there will be a difference of 0.1 or less between the refractive indices of the organic-inorganic composite filler and a polymer of a polymerizable monomer used to form the dental curable composition. When the monomer is selected in such a manner, a transparent cured product can be obtained from the dental curable composition.

Based on 100 parts by mass of the inorganic primary particles, the content of the organic resin phase in the organic-inorganic composite filler is generally from 1 to 40 parts by mass, preferably from 5 to 25 parts by mass. The content of the organic resin phase can be determined from a weight reduction obtained by thermogravimetry-differential thermal analysis.

(Method of Manufacturing Organic-Inorganic Composite Filler)

Hereinafter, a description is given of methods of manufacturing the organic-inorganic composite filler of the present invention having intra-agglomerate voids. Methods of manufacturing the organic-inorganic composite filler of the present invention are not limited to specific methods. However, it is generally difficult to manufacture the organic-inorganic composite filler of the present invention using methods of manufacturing conventional organic-inorganic composite fillers.

Specifically, the organic-inorganic composite filler of the present invention is preferably manufactured by the method described below. This method essentially includes using inorganic agglomerated particles of inorganic primary particles with an average particle size of 10 to 1,000 nm as a starting material and performing the steps described below.

(1) The step of impregnating the inorganic primary particles with a polymerizable monomer solution containing 100 parts by mass of an organic solvent, 3 to 70 parts by mass of a polymerizable monomer, and an effective amount of a polymerization initiator.

(2) The step of removing the organic solvent from inorganic agglomerated particles.

(3) The step of polymerizing and curing the polymerizable monomer with which the inorganic agglomerated particles are impregnated.

In the manufacturing method, inorganic agglomerated particles, which consist of agglomerates of inorganic primary particles with an average particle size of 10 to 1,000 nm, are first prepared as a starting material. For example, when manufactured by a wet method, the inorganic primary particles can be obtained in the form of strong agglomerates of particles, and even when manufactured by a dry method, they can be obtained in the form of weak agglomerates of particles. Also when manufactured by a sol-gel method, the inorganic primary particles are usually agglomerated in a drying or firing process. In the present invention, if necessary, the inorganic agglomerated particles obtained in such a manner may be ground before use. In some cases, however, the grinding may be inappropriate, because it will be difficult for the grinding to control the particle size of the inorganic agglomerated particles, so that the resulting inorganic agglomerated particles will have a broad particle size distribution.

To avoid such an inappropriate situation, inorganic agglomerated particles obtained by granulation using a spray drying method are preferably used as a starting material in the manufacturing of the organic-inorganic composite filler. As used herein, the term "spray drying method" is intended to include a method of making inorganic agglomerated particles, which includes: spraying a slurry into fine droplets, for example, using a fast gas stream, wherein the slurry is a dispersion of inorganic primary particles in a volatile liquid medium such as water; and bringing the sprayed droplets into contact with high-temperature gas to volatilize the liquid medium so that a large number of inorganic primary particles dispersed in droplets are gathered into substantially a single agglomerate particle. The particle size or particle size distribution of the agglomerate particles is controlled depending on the type of spray or the spray conditions.

The method of granulation by a spray drying method is advantageous, because it can produce inorganic agglomerated particles with a narrow particle size distribution and an average particle size of 3 to 100 μm, which is a desired particle size for the organic-inorganic composite filler. Additionally, in such inorganic agglomerated particles, intra-agglomerate voids are spontaneously formed with a pore volume of 0.015 to 0.35 $cm^3/g$, more preferably 0.15 to 0.30 $cm^3/g$, as measured by mercury intrusion porosimetry. When the organic-inorganic composite filler is manufactured using inorganic agglomerated particles agglomerated in such a manner, intra-agglomerate voids are generally formed with a pore volume of 0.01 to 0.30 $cm^3/g$, more preferably 0.03 to 0.20 $cm^3/g$, in the inside of the resulting organic-inorganic composite filler. Therefore, when the inorganic agglomerated particles manufactured by the above method are used as a starting material, the organic-inorganic composite filler of the present invention can be obtained efficiently.

In general, the pore volume of inorganic agglomerated particles increases with narrowing the particle size distribution of inorganic primary particles used to form the inorganic agglomerated particles, and decreases with broadening the particle size distribution of the inorganic primary particles. In addition, the pore volume of inorganic agglomerated particles can be reduced using a combination of different types of inorganic primary particles with different average particle sizes. Moreover, the pore volume of inorganic agglomerated particles can be further reduced using a combination of two or more types of inorganic primary particles in such a manner that close packing can be achieved.

Preferred spray drying methods are specifically described. A method includes dispersing inorganic particles in an appropriate solvent such as water to form a slurry and finely spraying the slurry using a fast gas stream to dry the particles. Another method includes allowing drops of a slurry to fall on a rotating disk so that the slurry is flicked and sprayed by the centrifugal force to dryness. Examples of the solvent include water, ethanol, isopropyl alcohol, chloroform, and dimethylformamide.

The concentration of inorganic particles in the slurry is generally from 5 to 50% by mass, preferably from 10 to 45% by mass, while it is not restricted as long as the slurry can be sprayed using a fast gas stream or a rotating disk. The rotational speed of the rotating disk is generally from 1,000 to 50,000 rpm. The droplet size is so controlled that inorganic agglomerated particles with the desired average particle size can be obtained, taking into account the inorganic primary particle size.

When the sprayed slurry is immediately dried using high-temperature air or inert gas, inorganic agglomerated particles with uniform size can be obtained. The temperature of the gas used in the drying is generally from 60 to 300° C., preferably from 80 to 250° C.

A slight amount of the solvent, which is used in the preparation of the slurry, may still remain in the inorganic agglomerated particles obtained by the spray drying. Therefore, after the spray drying, the resulting inorganic agglomerated particles are preferably dried under vacuum. The vacuum drying is generally performed for a time period of 1 to 48 hours at a temperature of 20 to 150° C. under a reduced pressure of 0.01 to 100 hPa or less.

The inorganic agglomerated particles obtained by the spray drying generally have a spherical shape, a near-spherical shape, a toroidal shape, or a dimpled shape having dimples on the surface of the particle. The inorganic agglomerated particles are generally obtained in the form of a mixture of two or more of these inorganic agglomerated particle shapes. Therefore, the organic-inorganic composite filler manufactured using such a mixture of inorganic agglomerated particles generally has the corresponding shapes.

The inorganic agglomerated particles with a spherical shape, a near-spherical shape, or the like tend to form a hollow structure. The curing product of a curable composition containing an organic-inorganic composite filler with a hollow structure tends to have somewhat reduced mechanical strength. In the process of preparing a curable composition, however, a large amount of a polymerizable monomer can be allowed to selectively penetrate and fill the hollow part, so that the light diffusion properties can be modified. This effect can be advantageously used in dental applications.

In general, when the concentration of the slurry used in the spray drying is set relatively high and when the sprayed slurry droplets are dried by hot blast in a relatively short time, spherical or near-spherical inorganic agglomerated particles are manufactured in a large amount, in which the content of the inorganic agglomerated particles with a hollow structure tends to decrease. On one hand, as the slurry concentration decreases, the content of the manufactured toroidal or dimpled inorganic agglomerated particles tends to increase, and the content of the hollow inorganic agglomerated particles in the spherical or near-spherical inorganic agglomerated particles tends to increase.

When inorganic primary particles with an average particle size of 10 to 1,000 nm are granulated by a spray drying method, inorganic agglomerated particles can be manufactured having intra-agglomerate voids with a pore volume of 0.015 to 0.35 cm$^3$/g, more preferably 0.15 to 0.30 cm$^3$/g. In such inorganic agglomerated particles, inorganic primary particles agglomerated near the surface generally have an arrangement close to a hexagonal close-packed structure. When inorganic primary particles with an average particle size of 10 to 1,000 nm are arranged along the surface of the inorganic agglomerated particles to form a structure close to a hexagonal close-packed structure, pores are formed by intra-agglomerate voids, which are formed between adjacent inorganic primary particles. Such pores usually have an average pore size of 5 to 330 nm, more usually 20 to 300 nm.

The pore volume and the average pore size of the inorganic agglomerated particles can be determined by the same measurement method as in the case of the organic-inorganic composite filler described above.

The inorganic agglomerated particles to be used in the manufacturing of the organic-inorganic composite filler are preferably surface-treated with a hydrophobing agent so as to have increased wettability to the polymerizable monomer. Any known hydrophobing agent may be used without restriction. Preferred examples of the hydrophobing agent include silane coupling agents such as vinyltriethoxysilane, vinyltrimethoxysilane, vinyl-tris(β-methoxyethoxy) silane, γ-methacryloyloxypropyltrimethoxysilane, κ-methacryloyloxydodecyltrimethoxysilane, β-(3,4-epoxycyclohexyl)-ethyltrimethoxysilane, γ-glycidoxypropyl-trimethoxysilane, N-β-(aminoethyl)-γ-aminopropyl-trimethoxysilane, γ-ureidopropyl-triethoxysilane, γ-chloropropyltrimethoxysilane, methyltrimethoxysilane, ethyltrimethoxysilane, and methyltriethoxysilane, and titanate coupling agents.

The amount of the hydrophobing agent used for hydrophobing the inorganic agglomerated particles is not particularly restricted and may be set at an optimal value after a preliminary experiment is performed to check the mechanical properties and other properties of the organic-inorganic composite filler to be obtained. For example, the hydrophobing agent is preferably used in an amount of 1 to 30 parts by mass based on 100 parts by mass of the inorganic primary particles.

The surface treatment method is not particularly restricted, and any known surface treatment method may be used without restriction. A typical treatment method includes dispersing and mixing inorganic particles and a hydrophobing agent in an appropriate solvent using a ball mill or the like, removing the solvent by drying using an evaporator or air drying, and then performing heating at 50 to 150° C. Another treatment method includes heating and refluxing inorganic particles and a hydrophobing agent in a solvent such as alcohol or the like for several hours or so. A further treatment method includes graft-polymerizing a hydrophobing agent onto the particle surfaces.

The surface treatment may be performed on the inorganic primary particles or the inorganic agglomerated particles. When the inorganic agglomerated particles are manufactured by the spray drying, it is efficient to perform the surface treatment at the same time in this process.

Subsequently, the inorganic agglomerated particles manufactured as described above are immersed in a polymerizable monomer solution containing 100 parts by mass of an organic solvent, 3 to 70 parts by mass of a polymerizable monomer, and an effective amount of a polymerization initiator. As a result, the polymerizable monomer solution penetrates the inside of the inorganic agglomerated particles through the intra-agglomerate voids of the inorganic agglomerated particles by capillarity. In this case, since the polymerizable monomer is diluted with the organic solvent, the liquid can highly penetrate by capillarity. Therefore, even deeper parts of the intra-agglomerate voids are filled with the polymerizable monomer solution.

The content of the polymerizable monomer in the polymerizable monomer solution based on the amount of the organic solvent needs to be controlled in the above range. When the content of the polymerizable monomer is controlled in the range, the volume of the pores formed by the intra-agglomerate voids of the resulting organic-inorganic composite filler can be controlled in the specified range. The organic solvent in the polymerizable monomer solution, which penetrates the intra-agglomerate voids of the inorganic agglomerated particles, is removed before the polymerization and curing of the polymerizable monomer. Pores having a volume corresponding to the reduction in volume caused by the removal of the solvent are formed in the intra-agglomerate voids of the inorganic primary particles. For this reason, the concentration of the polymerizable monomer in the polymerizable monomer solution should be as stated above so that the organic-inorganic composite filler can have a pore volume in the above range (0.01-0.30 cm$^3$/g).

If the polymerizable monomer content is out of the range, the amount of the polymerizable monomer charged into the pores may be excessive or insufficient. If the polymerizable monomer content is too high, air bubbles may be formed in the filler. In addition, the excessive polymerizable monomer may adhere to the circumference of the inorganic agglomerated particles, so that a problem may easily occur, such as the manufacturing of a block of inorganic agglomerated particles bonded together. Taking such a problem into account, the content of the polymerizable monomer in the polymerizable monomer solution is preferably from 10 to 50 parts by mass based on 100 parts by mass of the organic solvent.

Any known organic solvent may be used in the polymerizable monomer solution. Examples include halogen-based organic solvents such as perchloroethylene, trichloroethylene, dichloromethane, and chloroform. Further examples include halogen-free organic solvents including hydrocarbons such as hexane, heptane, and pentane; aromatic compounds such as benzene, toluene, and xylene; alcohol compounds such as methanol, ethanol, 1-propanol, 2-propanol, 1-butanol, and 2-butanol; ether compounds such as diethyl ether, tetrahydrofuran, and tert-butyl methyl ether; ketone compounds such as acetone, methyl ethyl ketone, and methyl isobutyl ketone; and ester compounds such as ethyl formate, methyl acetate, ethyl acetate, propyl acetate, and isopropyl acetate. Among these solvents, methanol, ethanol, acetone, dichloromethane, and the like are more preferred, because they are highly volatile so that the time for the solvent removal step can be reduced, easily available and inexpensive, and highly safe to the human body during the process.

The polymerization initiator contained in the polymerizable monomer solution may be any of a photopolymerization initiator, a chemical polymerization initiator, and a thermal polymerization initiator. A photopolymerization initiator or a thermal polymerization initiator is preferred, because energy such as light or heat can be applied from the outside so that the timing of the polymerization can be freely selected and the manufacturing operation can be made simple. A thermal polymerization initiator is more preferred because it can be used without a process environment restriction such as light shielding or application of red light.

Examples of the thermal polymerization initiator include a peroxide such as benzoyl peroxide, p-chlorobenzoyl peroxide, tert-butylperoxy-2-ethylhexanoate, tert-butylperoxydicarbonate, or diisopropylperoxydicarbonate, an azo compound such as azobisisobutyronitrile, a boron compound such as tributyl borane, a partial oxide of tributyl borane, sodium tetraphenylborate, sodium tetrakis(p-fluorophenyl)borate, or tetraphenylborate triethanolamine salt, barbituric acids such as 5-butylbarbituric acid and 1-benzyl-5-phenylbarbituric acid, and sulfinates such as sodium benzenesulfinate and sodium p-toluenesulfinate.

Among the above thermal polymerization initiators, an azo compound such as azobisisobutyronitrile is advantageously used, because it is highly safe during the operation and has little coloring effect on the organic-inorganic composite filler.

These polymerization initiators may be used alone or in combination of two or more. The amount of the polymerization initiator may be an effective amount enough to allow the polymerization to proceed. Based on 100 parts by mass of the polymerizable monomer, the amount of the polymerization initiator is generally from 0.01 to 30 parts by mass, more preferably from 0.1 to 5 parts by mass.

To impart various functions to the organic-inorganic composite filler, additives such as an ultraviolet absorbing agent, a pigment, a dye, a polymerization inhibitor, and a fluorescent agent may be added to the polymerizable monomer solution.

For example, the polymerizable monomer solution is allowed to penetrate the inorganic agglomerated particles by a method of immersing the inorganic agglomerated particles in the polymerizable monomer solution. In general, the immersion is preferably performed at room temperature under normal pressure. The mixing ratio of the polymerizable monomer solution to the inorganic agglomerated particles is preferably from 30 to 500 parts by mass, more preferably 50 to 200 parts by mass of the polymerizable monomer solution to 100 parts by mass of the inorganic agglomerated particles. The mixture may be allowed to stand preferably for 30 minutes or more, more preferably for 1 hour or more. To accelerate the penetration of the polymerizable monomer solution into the intra-agglomerate voids, the mixture may be shaken and stirred, centrifuged and stirred, pressurized, reduced in pressure, or heated.

After the inorganic agglomerated particles are immersed in the polymerizable monomer solution, the organic solvent is removed from the polymerizable monomer solution charged in the intra-agglomerate voids before the polymerizable monomer is subjected to polymerization and curing. In the removal of the organic solvent, substantially the whole amount (generally, 95% by mass or more) of the organic solvent penetrating the intra-agglomerate voids of the inorganic agglomerated particles is removed. Visually, the removal may be performed until coagulates sticking together disappear so that flowing powder is obtained.

Any known drying method may be performed in the process of removing the organic solvent. Examples of the drying method include drying by heating, such as convective heat transfer drying, radiant heat transfer drying, conductive heat transfer drying, or internal heat generation drying, and drying without heating, such as vacuum drying, vacuum-freeze drying, spin drying, drying with an absorbent, suction drying, press drying, or ultrasonic drying. In particular, drying by heating, vacuum drying, vacuum-freeze drying, or the like is preferred.

When vacuum drying is performed, the reduced pressure may be appropriately selected taking into account the boiling point or volatility of the organic solvent. The reduced pressure is generally 100 hPa or less, preferably from 0.01 to 50 hPa, most preferably from 0.1 to 10 hPa.

When drying is performed by heating, the heating temperature may be appropriately selected depending on the boiling point of the organic solvent. When the organic solvent contains a thermal polymerization initiator, the heating should be performed at a temperature equal to or less than the polymerization-initiating temperature.

The drying method may be any combination of the above methods. In particular, to reduce the drying time, vacuum drying is preferably used in combination with drying by heating, such as conductive heat transfer drying. The process of removing the organic solvent may be performed under stirring, as long as the properties of the organic-inorganic composite filler are not degraded.

After the organic solvent is removed, the polymerizable monomer is subjected to polymerization and curing. The polymerization-curing method to be used depends on the polymerizable monomer or polymerization initiator used, and therefore, an optimal method should be selected as needed. When a thermal polymerization initiator is used, the polymerization is performed by heating, and when a photopolymerization initiator is used, the polymerization is performed by applying light with the corresponding wavelength.

When thermal polymerization is performed, the polymerization temperature depends on the polymerization initiator used, and therefore, an optimal temperature should be selected as desired. The polymerization temperature is generally from 30 to 170° C., preferably from 50 to 150° C.

When photopolymerization is performed, the light source to be used depends on the type of the polymerization initiator, and therefore, an optimal light source should be used as desired. The light source is generally a visible light source such as a halogen lamp, LED, a xenon lamp, a high-pressure mercury lamp, a metal halide lamp, a carbon arc lamp, a tungsten lamp, a helium-cadmium laser, or an argon laser, or an ultraviolet light source such as a low-pressure mercury lamp, a xenon arc lamp, a deuterium arc lamp, a mercury-xenon arc lamp, a tungsten-halogen incandescent lamp, UV-LED, or a xenon plasma discharge tube.

The method described above enables efficient manufacturing of the organic-inorganic composite filler having internal pores. The above processes may be repeated twice or more depending on the concentration or other properties of the polymerizable monomer solution. When the processes are repeated twice or more, the amount of the organic resin covering the surfaces of the inorganic primary particles can be increased, so that the volume of the pores formed can be controlled.

The resulting organic-inorganic composite filler may be directly used as a final product, if it is manufactured using inorganic agglomerated particles with adequate particles sizes. Inorganic agglomerated particles granulated by the spray drying method are such inorganic agglomerated particles with adequate particle sizes. When the resulting organic-inorganic composite filler has a too large particle size, the filler may be ground into an appropriate size, if necessary. The grinding can be performed using a vibratory ball mill, a bead mill, a jet mill, or the like. If necessary, classification may also be performed using sieves, an air classifier, a hydraulic classifier, or the like. The time when the grinding process is performed may be after the impregnation of the inorganic agglomerated particles with the polymerizable monomer solution and the removal of the organic solvent and before the polymerization of the polymerizable monomer.

The organic-inorganic composite filler may also be surface-treated. When a surface treatment is performed, the curing product of a dental curable composition containing the organic-inorganic composite filler can have higher mechanical strength. The surface treatment agent and the surface treatment method may be those described above for the surface treatment of inorganic primary particles.

(Dental Curable Composition)

As described above, the organic-inorganic composite filler of the present invention is particularly useful as a dental filler to be added to a dental curable composition. Such a dental curable composition contains a polymerizable monomer and a polymerization initiator in addition to the organic-inorganic composite filler.

Any known polymerizable monomer used in such applications may be used without restriction. In general, it may be selected from the same group as described above for the polymerizable monomer for use in the manufacturing of the organic-inorganic composite filler. The polymerizable monomer may be added in an amount of 10 to 100 parts by mass, preferably 20 to 80 parts by mass, based on 100 parts by mass of the organic-inorganic composite filler.

Any known polymerization initiator may be used without restriction. For example, the thermal polymerization initiator and so on described above for the polymerization and curing of the monomer penetrating the inorganic agglomerated particles may be used. In general, photopolymerization is frequently used to cure (polymerize) dental curable compositions, because the operation is simple during its use. For this reason, a photopolymerization initiator is also preferably used in the dental curable composition of the present invention.

Preferred examples of the photopolymerization initiator include benzoinalkyl ethers, benzyl ketals, benzophenones, α-diketones, thioxanthone compounds, and bisacylphosphine oxides. A reducing agent is often added to the photopolymerization initiator. Examples of such a reducing agent include aromatic amines, aliphatic amines, aldehydes, and sulfur-containing compounds. If necessary, a trihalomethyltriazine compound, an aryliodonium salt, or the like may also be added. The polymerization initiator is generally added in an amount of 0.01 to 10 parts by mass based on 100 parts by mass of the polymerizable monomer.

Any other inorganic filler may also be added to the dental curable composition as long as the effects of the present invention are not impaired. Any other known inorganic filler used in such applications may be used without restriction. For example, any other inorganic filler may be inorganic particles made of the same material as the above inorganic primary particles.

Any known additive may also be added to the dental curable composition of the present invention as long as the effects are not significantly interfered with. Examples of such an additive include a polymerization inhibitor, a pigment, an ultraviolet absorbing agent, a fluorescent agent, etc.

The dental curable composition of the present invention can be generally manufactured by a process including sufficiently kneading predetermined amounts of the respective essential components and any optional additive component (s) to form a paste and degassing the paste under reduced pressure to remove air bubbles. While the dental curable composition may be used for any applications, particularly preferred applications include dental composite restorative materials such as dental restorative filling materials and indirect dental restorative materials.

EXAMPLES

Hereinafter, the present invention is more specifically described with reference to examples, which however are not intended to limit the present invention. Listed below are abbreviations for compounds used in the examples and the comparative examples, such as polymerizable monomers, inorganic particles, and polymerization initiators.

A) Polymerizable Monomers
3G: Triethylene glycol dimethacrylate
HD: 1,6-hexanediol dimethacrylate
GMA: 2,2-bis[(3-methacryloyloxy-2-hydroxypropyloxy)phenyl]propan UDMA: 1,6-bis(methacrylethyloxycarbonylamino)-2,2-4-trimethylhexane
D2.6E: Compound represented by the following formula:

[Chemical Formula 1]

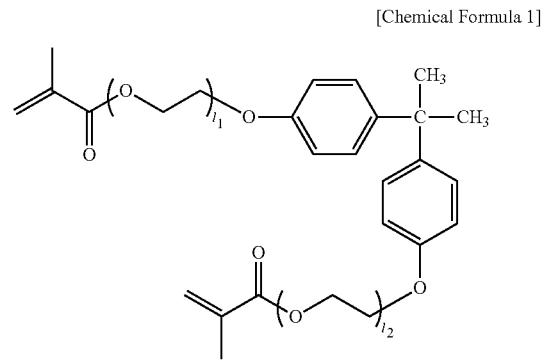

* A mixture in which the average ($l_1+l_2$) is 2.6.
Abbreviations for inorganic particles are listed below.
B) Inorganic Particles
F-1: Spherical (average degree of symmetry 0.95) primary particles of silica-zirconia with an average particle size of 200 nm manufactured by sol-gel method
F-2: Spherical (average degree of symmetry 0.95) primary particles of silica-zirconia with an average particle size of 400 nm manufactured by sol-gel method
F-3: Spherical (average degree of symmetry 0.95) primary particles of silica-zirconia with an average particle size of 70 nm manufactured by sol-gel method
F-4: Spherical (average degree of symmetry 0.95) primary particles of silica-titania with an average particle size of 80 nm manufactured by sol-gel method
F-5: Spherical (average degree of symmetry 0.95) primary particles of silica-zirconia with an average particle size of 700 nm manufactured by sol-gel method F-6: Irregular form primary particles of silica-zirconia with an average particle size of 200 nm manufactured by sol-gel method F-7: Near-spherical (average degree of symmetry 0.60) primary particles of alumina with an average particle size of 200 nm manufactured by high-temperature melting method F-8: Irregular form primary particles of silica-zirconia with an average particle size of 2,000 nm manufactured by sol-gel method F-9: Spherical (average degree of symmetry 0.95) primary particles of silica-zirconia with an average particle size of 50 nm manufactured by sol-gel method F-10: Near-spherical (average degree of symmetry 0.60) primary particles of ytterbium trifluoride with an average particle size of 50 nm manufactured by sol-gel method Abbreviations for polymerization initiators are listed below.

C) Polymerization Initiators
AIBN: Azobisisobutyronitrile
CQ: Camphorquinone
DMBE: Ethyl N,N-dimethyl-p-benzoate The methods described below were used to determine the average particle size and average degree of symmetry of the inorganic primary particles, the properties (average particle size, pore volume, and average pore size) of the inorganic agglomerated particles and the organic-inorganic composite filler, and the content of organic resin in the organic-inorganic composite filler, and the bending strength, and to evaluate the transparency.

(1) Average Particle Size and Average Degree of Symmetry of Inorganic Primary Particles Constituting Organic-Inorganic Composite Filler The organic-inorganic composite filler was photographed at a magnification of 5,000 to 100,000 times using a scanning electron microscope (XL-30S FEG, manufactured by PHILIPS). Using image analysis software (IP-1000PC, manufactured by Asahi Kasei Engineering Corporation), the image was processed, and the circle-equivalent diameter (particle size), maximum length, minimum width, and number of primary particles in a unit field were determined. The number of the particles observed was at least 100. The average volume diameter of the primary particles was calculated using the formula below and used as the average particle size.

$$\text{Average particle size: } X = \sqrt[3]{\frac{\sum_{i=1}^{n} X_i^3}{n}} \text{ (average volume diameter)} \quad \text{[Formula 3]}$$

n: the number of observed particles
Xi: the particle size (diameter) of the i-th particle The number (n) of the primary particles observed in a unit field, the long diameter (Li) (the maximum length of the primary particle), and the minimum width (Bi) (the diameter in the direction perpendicular to the long diameter) were also determined. The average degree of symmetry of the inorganic primary particles was calculated using the formula below.

$$\text{Average degree of symmetry} = \frac{\sum_{i=1}^{n} Bi/Li}{n} \quad \text{[Formula 4]}$$

(2) Average Particle Size (Grain Size) of Inorganic Agglomerated Particles

In 10 ml of ethanol were dispersed 0.1 g of inorganic agglomerated particles and sufficiently shaken by hand. The dispersion was analyzed by laser diffraction/scattering method using a particle size distribution meter (LS230, manufactured by Beckman Coulter, Inc.), and the median diameter was determined by calculation of volume statistics using an optical model (Fraunhofer).

(3) Average Particle Size (Grain Size) of Organic-Inorganic Composite Filler

The particle size was determined by the same procedure as in the case of (2) inorganic agglomerated particles, except that supersonic wave was applied for 20 minutes in the process of dispersing the organic-inorganic composite filler in ethanol.

(4) Pore Volume and Average Pore Size of the Intra-Agglomerate Voids in Inorganic Agglomerated Particles and Organic-Inorganic Composite Filler The pore volume distribution was measured using a mercury porosimeter (PoreMaster, manufactured by Quantachrome Instruments). To a measurement cell was added 0.2 g of the inorganic agglomerated particles or the organic-inorganic composite filler and subjected to the measurement. The pore volumes within the pore size range of 1 to 500 nm in the pore volume distribution were summed to determine the pore volume. Concerning the pores in this range, the median pore diameter was also calculated from the pore volume distribution and used as the average pore size of the intra-agglomerate voids.

(5) Content of Organic Resin in Organic-Inorganic Composite Filler

The organic resin content was determined by the procedure described below using a thermogravimetry/differential thermal analyzer (TG/DTA 6300, manufactured by SII NanoTechnology Inc.). In an aluminum pan was placed 0.03 g of the organic-inorganic composite filler as a sample. Heating was performed according to the schedule: a rate of temperature increase of 5° C./minute, an upper limit temperature of 500° C., and an upper limit temperature holding time of 30 minutes, while the weight reduction was measured. Using the resulting weight reduction, the weight ratio of the organic resin and the inorganic particles was calculated, and the amount (parts by mass) of the organic resin based on 100 parts by mass of the inorganic particles was calculated. In the thermogravimetry/differential thermal analysis, 0.03 g of aluminum oxide was used as a reference material.

(6) Method of Measuring Bending Strength

According to the formulation below, an organic matrix containing polymerizable monomers and a photopolymerization initiator was mixed with predetermined amount of an inorganic filler and the organic-inorganic composite filler prepared in each of the examples and the comparative examples. Under red light, the mixture was uniformly kneaded in the mortar, and degassed to form a dental curable paste composition.

3G 40 parts by mass
GMA 60 parts by mass
CQ 0.20 parts by mass
DMBE 0.35 parts by mass
Organic-inorganic composite filler 240 parts by mass
F-1 160 parts by mass Using a filling instrument, a paste of this dental curable composition was filled into a stainless steel frame mold. A polypropylene sheet was pressed against the surface of the paste, and the paste was irradiated with light through the polypropylene sheet. The irradiation was performed using a visible ray irradiator Powerlight (manufactured by Tokuyama Dental Corporation). The irradiation window of the visible ray irradiator was brought into contact with the polypropylene sheet, and one side was irradiated three times for 30 seconds each from different locations in such a manner that the curable material was entirely irradiated with light. Subsequently, the other side was also irradiated in the same manner three times for 30 seconds each, so that a cured product was obtained.

The cured product was shaped into a rectangular prism of 2×2×25 mm using waterproof abrasive paper #800. The resulting sample piece was mounted on a tester (Autograph AG5000D, manufactured by SHIMADZU CORPORATION) and measured for three-point bending fracture strength under the testing conditions of a support distance of 20 mm and a cross-head speed of 1 mm/minute. Five test pieces were evaluated, and the average value was used as the bending strength.

(7) Evaluation of Transparency

A paste of the same dental curable composition as prepared by the method (6) was filled into a mold having a hole of 7 mmϕ×1 mm. Polyester films were pressed against the surfaces of the paste at both ends of the hole. Both surfaces of the paste were irradiated with light from a visible ray irradiator (Powerlight, manufactured by Tokuyama Dental Corporation) for 30 seconds through the polyester films. After cured, the paste cured was taken out from the mold. The tristimulus Y value of the cured paste (background color: black and white) was measured using a color-difference meter (TC-1800MK-II, manufactured by Tokyo Denshoku Co., Ltd.). The contrast ratio was calculated from the following formula and used as a measure of transparency.

contrast ratio=($Y$ value in the case of black background)/($Y$ value in the case of white background)

Example 1

One hundred g of inorganic particles F-1 were added to 200 g of water, and a dispersion of the inorganic particles was obtained by using a circulating bead mill SC Mill (manufactured by Mitsui Mining Company, Ltd.).

Subsequently, 4 g (0.016 mol) of γ-methacryloyloxypropyltrimethoxysilane and 0.003 g of acetic acid were added to 80 g of water, and stirred for 1 hour and 30 minutes, so that a uniform solution with a pH of 4 was obtained. The solution was added to the inorganic particle dispersion and mixed uniformly. Thereafter, while lightly stirred, the dispersion was supplied onto a disk rotating at high speed and dried by spray drying method.

The spray drier used had a rotary disk, in which atomization was performed by centrifugal force (Spray Drier TSR-2W, manufactured by Sakamoto Giken K.K.). The rotational speed of the disk was 10,000 rpm, and the temperature of the air of the drying atmosphere was 200° C. Subsequently, the spray-dried inorganic powder was vacuum-dried at 60° C. for 18 hours, so that 71 g of inorganic agglomerated particles were obtained. The intra-agglomerate voids of the inorganic agglomerated particles had a pore volume of 0.25 cm$^3$/g and an average pore size of 50 nm. The inorganic agglomerated particles had an average particle size of 40.0 μm.

Subsequently, 0.64 g of GMA, 0.43 g of 3G, and 0.71 g of HD as polymerizable monomers, 0.005 g of AIBN as a polymerization initiator, and 5.0 g of methanol as an organic solvent were mixed to form a polymerizable monomer solution (containing 35.6 parts by mass of the polymerizable monomers based on 100 parts by mass of the organic solvent), and then 10.0 g of the inorganic agglomerated particles were immersed in the polymerizable monomer solution. The mixture was sufficiently stirred and allowed to stand for 1 hour after it was confirmed that the mixture was turned into a slurry.

With stirring, the mixture was dried for 1 hour under the conditions of a reduced pressure of 10 hPa and a heating temperature of 40° C. (warm water bath temperature) using a rotary evaporator, so that the organic solvent was removed. After the removal of the organic solvent, a non-cohesive, highly-fluid powder was obtained.

While stirred in a rotary evaporator, the powder was heated for 1 hour under the conditions of a reduced pressure of 10 hPa and a heating temperature of 100° C. (oil bath temperature) so that the polymerizable monomers in the powder were polymerized and cured, and as a result, 8.5 g of an organic-inorganic composite filler was obtained. The intra-agglomerate voids of the organic-inorganic composite filler had a pore volume of 0.09 cm$^3$/g and an average pore size of 30 nm. The organic-inorganic composite filler had an average particle size of 40.4 μm, and it was also confirmed that the inorganic primary particles of the filler had an average particle size of 200 nm. The content of the organic resin in the organic-inorganic composite filler was also determined to be 17.4 parts by mass based on 100 parts by mass of the inorganic particles F-1.

Example 2

Using the same process as in Example 1, 66 g of inorganic agglomerated particles were obtained, except that 70 g of inorganic particles F-2 and 30 g of inorganic particles F-3 were added to 200 g of water when a dispersion was obtained by using a circulating bead mill SC Mill. The intra-agglomerate voids of the resulting inorganic agglomerated particles had a pore volume of 0.20 cm$^3$/g and an average pore size of 35 nm. The inorganic agglomerated particles had an average particle size of 33.7 μm.

Subsequently, 8.1 g of an organic-inorganic composite filler was manufactured using the inorganic agglomerated particles by the same process as in Example 1. The intra-agglomerate voids of the organic-inorganic composite filler had a pore volume of 0.04 cm$^3$/g and an average pore size of 14 nm. The inorganic agglomerated particles had an average particle size of 34.2 μm, and it was also confirmed that the inorganic primary particles of the agglomerate particles had an average particle size of 400 nm. The content of the organic resin in the organic-inorganic composite filler was also determined to be 17.4 parts by mass based on 100 parts by mass of the inorganic particles F-2.

Examples 3-16

Organic-inorganic composite fillers were obtained as in Example 1, except that the type of the inorganic particles used in the manufacturing of the inorganic agglomerated particles and the type and amount of the polymerizable monomers and the polymerization initiator in the polymerizable monomer solution were each changed as shown in Table 1, and the physical properties of each product were measured as in Example 1. The results are shown together in Table 1.

Comparative Example 1

The same inorganic agglomerated particles as in Example 1, 12 g of GMA, 8 g of 3G, and 13.3 g of HD as polymerizable monomers, and 0.10 g of AIBN as a polymerization initiator were each added to a mortar and mixed together to form a mixture paste. The mixture paste was degassed under reduced pressure and then subjected to polymerization and curing at 100° C. for 30 minutes. The cured product was ground in a vibratory ball mill (zirconia ball diameter: 5 mm), and the ground product was sieved so that particles with sizes of 100 µm or more were removed. The resulting organic-inorganic composite filler had an average particle size of 20.3 µm. Pores were not confirmed by the measurement with a mercury porosimeter. The content of the organic resin in the organic-inorganic composite filler was determined to be 33.0 parts by mass based on 100 parts by mass of the inorganic particles F-1.

Comparative Examples 2-5

Organic-inorganic composite fillers were obtained as in Example 1, except that the type of the inorganic particles used in the manufacturing of the inorganic agglomerated particles and the type and amount of the polymerizable monomers and the polymerization initiator in the polymerizable monomer solution were each changed as shown in Table 2. The physical properties of each of the organic-inorganic composite fillers were measured as in Example 1. The results are shown together in Table 2. Examples 17-32 and Comparative Examples 6-10

Each dental curable composition was prepared using each organic-inorganic composite filler as shown in Table 3, and the measurement of the bending strength and the evaluation of the transparency were performed. The results are shown together in Table 3.

TABLE 1

| | Inorganic agglomerated particles | | | | Formulation of polymerizable monomer solution | | | | | Organic-inorganic composite filler | | | | |
|---|---|---|---|---|---|---|---|---|---|---|---|---|---|---|
| | | | | | Components of polymerizable monomer solution | | | | Amount (parts by mass) of polymerizable monomer solution based on 100 parts by mass of inorganic agglomerated particles | | | | Amount (parts by mass) of organic resin based on 100 parts by mass of inorganic particles | |
| | Inorganic particles/parts by mass | Pore volume (cm³/g) | Average pore size (nm) | Average particle size (μm) | Organic solvent/parts by mass | Polymerizable monomer/parts by mass | Polymerization initiator/parts by mass | Amount (parts by mass) of polymerizable monomers based on 100 parts by mass of organic solvent | | Pore volume (cm³/g) | Average pore size (nm) | | Average particle size (μm) |
| Example 1 | F-1/100 | 0.25 | 50 | 40.0 | Methanol/100 | GMA/12.8 3G/8.6 HD/14.2 | AIBN/0.10 | 35.6 | 67.9 | 0.09 | 30 | 17.4 | 40.4 |
| Example 2 | F-2/70 F-3/30 | 0.17 | 35 | 33.7 | Methanol/100 | GMA/12.8 3G/8.6 HD/14.2 | AIBN/0.10 | 35.6 | 67.9 | 0.04 | 14 | 17.4 | 34.2 |
| Example 3 | F-4/100 | 0.24 | 33 | 38.6 | Methanol/100 | GMA/12.8 3G/8.6 HD/14.2 | AIBN/0.10 | 35.6 | 67.9 | 0.08 | 13 | 17.4 | 38.9 |
| Example 4 | F-5/100 | 0.33 | 250 | 42.3 | Methanol/100 | GMA/12.8 3G/8.6 HD/14.2 | AIBN/0.10 | 35.6 | 67.9 | 0.17 | 180 | 17.5 | 42.5 |
| Example 5 | F-6/100 | 0.35 | 180 | 37.2 | Methanol/100 | GMA/12.8 3G/8.6 HD/14.2 | AIBN/0.10 | 35.6 | 67.9 | 0.19 | 130 | 17.5 | 38.3 |
| Example 6 | F-7/100 | 0.25 | 60 | 35.5 | Methanol/100 | GMA/12.8 3G/8.6 HD/14.2 | AIBN/0.10 | 35.6 | 67.9 | 0.09 | 25 | 17.4 | 36.0 |
| Example 7 | F-1/100 | 0.25 | 50 | 40.0 | Methanol/100 | GMA/19.4 3G/13 HD/21.6 | AIBN/0.15 | 54.0 | 77.1 | 0.02 | 7 | 27.0 | 42.3 |
| Example 8 | F-5/100 | 0.33 | 250 | 42.3 | Methanol/100 | GMA/2.8 3G/2.0 HD/3.2 | AIBN/0.02 | 8.0 | 54.0 | 0.28 | 240 | 4.2 | 42.3 |
| Example 9 | F-1/100 | 0.25 | 50 | 40.0 | Methanol/100 | GMA/21.1 3G/14.2 HD/23.4 | AIBN/0.16 | 58.7 | 47.9 | 0.09 | 31 | 17.6 | 40.3 |
| Example 10 | F-1/100 | 0.25 | 50 | 40.0 | Methanol/100 | GMA/3.2 3G/2.2 HD/3.6 | AIBN/0.03 | 9.0 | 217.9 | 0.07 | 20 | 17.3 | 40.4 |

TABLE 1-continued

| | Inorganic agglomerated particles | | | | Formulation of polymerizable monomer solution | | | | | Organic-inorganic composite filler | | | |
|---|---|---|---|---|---|---|---|---|---|---|---|---|---|
| | | | | | Components of polymerizable monomer solution | | | Amount (parts by mass) of polymerizable monomer solution based on 100 parts by mass of inorganic agglomerated particles | | | | | |
| | Inorganic particles/parts by mass | Pore volume (cm³/g) | Average pore size (nm) | Average particle size (μm) | Organic solvent/parts by mass | Polymerizable monomer/parts by mass | Polymerization initiator/parts by mass | Amount (parts by mass) of polymerizable monomers based on 100 parts by mass of organic solvent | | Pore volume (cm³/g) | Average pore size (nm) | Amount (parts by mass) of organic resin based on 100 parts by mass of inorganic particles | Average particle size (μm) |
| Example 11 | F-1/100 | 0.25 | 50 | 40.0 | Methanol/100 | GMA/1.16 3G/0.76 HD/14.2 | AIBN/0.008 | 3.2 | 25.8 | 0.25 | 48 | 1.2 | 40.0 |
| Example 12 | F-1/100 | 0.25 | 50 | 40.0 | Ethanol/100 | GMA/12.8 3G/8.6 HD/14.2 | AIBN/0.10 | 35.6 | 67.9 | 0.09 | 30 | 17.5 | 40.5 |
| Example 13 | F-1/100 | 0.25 | 50 | 40.0 | Dichloromethane/100 | GMA/6.4 3G/4.3 HD/7.1 | AIBN/0.05 | 17.8 | 117.9 | 0.09 | 32 | 17.5 | 40.4 |
| Example 14 | F-1/100 | 0.25 | 50 | 40.0 | Methanol/100 | 3G/14.2 UDMA/8.6 D2.6E/12.8 | AIBN/0.10 | 35.6 | 67.9 | 0.09 | 28 | 17.3 | 40.4 |
| Example 15 | F-9/100 | 0.22 | 30 | 32.5 | Methanol/100 | GMA/12.8 3G/8.6 HD/14.2 | AIBN/0.10 | 35.6 | 67.9 | 0.07 | 12 | 17.3 | 33.0 |
| Example 16 | F-10/100 | 0.23 | 30 | 34.2 | Methanol/100 | GMA/12.8 3G/8.6 HD/14.2 | AIBN/0.10 | 35.6 | 67.9 | 0.08 | 12 | 17.3 | 34.5 |

TABLE 2

| | Inorganic agglomerated particles | | | | Formulation of polymerizable monomer solution Components of polymerizable monomer solution | |
|---|---|---|---|---|---|---|
| | Inorganic particles/parts by mass | Pore volume ($cm^3/g$) | Average pore size (nm) | Average particle size (μm) | Organic solvent/parts by mass | Polymerizable monomer/parts by mass |
| Comparative Example 1 | F-1/100 | 0.25 | 50 | 40.0 | — | GMA/12 3G/8 HD/13.3 |
| Comparative Example 2 | F-1/100 | 0.25 | 50 | 40.0 | Methanol/100 | GMA/17 3G/11.4 HD/19 |
| Comparative Example 3 | F-1/100 | 0.25 | 50 | 40.0 | Methanol/100 | GMA/0.85 3G/0.57 HD/0.95 |
| Comparative Example 4 | F-1/100 | 0.25 | 50 | 40.0 | Methanol/100 | GMA/32 3G/21.5 HD/35.5 |
| Comparative Example 5 | F-8/100 | 0.56 | 450 | 40.0 | Methanol/100 | GMA/12.8 3G/8.6 HD/14.2 |

| | Formulation of polymerizable monomer solution | | | Organic-inorganic composite filler | | | |
|---|---|---|---|---|---|---|---|
| | Components of polymerizable monomer solution | | | | | | |
| | Polymerization initiator/parts by mass | Amount (parts by mass) of polymerizable monomers based on 100 parts by mass of organic solvent | Amount (parts by mass) of polymerizable monomer solution based on 100 parts by mass of inorganic agglomerated particles | Pore volume ($cm^3/g$) | Average pore size (nm) | Amount (parts by mass) of organic resin based on 100 parts by mass of inorganic particles | Average particle size (μm) |
| Comparative Example 1 | AIBN/0.10 | — | — | 0.00 | 0 | 33.0 | 20.3 |
| Comparative Example 2 | AIBN/0.14 | 47.4 | 147.4 | 0.002 | 1 | 45.2 | 325.6 |
| Comparative Example 3 | AIBN/0.007 | 2.4 | 1023.7 | 0.003 | 1 | 24.1 | 43.5 |
| Comparative Example 4 | AIBN/0.25 | 89.0 | 37.8 | 0.002 | 1 | 17.2 | 250.2 |
| Comparative Example 5 | AIBN/0.10 | 35.6 | 67.8 | 0.40 | 410 | 17.3 | 43.3 |

TABLE 3

| | Organic-inorganic composite filler | Bending strength (MPa) | Transparency |
|---|---|---|---|
| Example 17 | Filler of Example 1 | 160 | 0.40 |
| Example 18 | Filler of Example 2 | 158 | 0.41 |
| Example 19 | Filler of Example 3 | 155 | 0.41 |
| Example 20 | Filler of Example 4 | 150 | 0.41 |
| Example 21 | Filler of Example 5 | 152 | 0.45 |
| Example 22 | Filler of Example 6 | 130 | 0.46 |
| Example 23 | Filler of Example 7 | 135 | 0.46 |
| Example 24 | Filler of Example 8 | 139 | 0.42 |
| Example 25 | Filler of Example 9 | 140 | 0.47 |
| Example 26 | Filler of Example 10 | 133 | 0.46 |
| Example 27 | Filler of Example 11 | 131 | 0.41 |
| Example 28 | Filler of Example 12 | 155 | 0.42 |
| Example 29 | Filler of Example 13 | 156 | 0.41 |
| Example 30 | Filler of Example 14 | 155 | 0.41 |
| Example 31 | Filler of Example 15 | 140 | 0.44 |
| Example 32 | Filler of Example 16 | 135 | 0.45 |
| Comparative Example 6 | Filler of Comparative Example 1 | 90 | 0.41 |
| Comparative Example 7 | Filler of Comparative Example 2 | 91 | 0.65 |
| Comparative Example 8 | Filler of Comparative Example 3 | 94 | 0.69 |
| Comparative Example 9 | Filler of Comparative Example 4 | 98 | 0.62 |
| Comparative Example 10 | Filler of Comparative Example 5 | 101 | 0.55 |

The invention claimed is:

1. A method for manufacturing a dental curable composition, comprising the steps:
   (A) manufacturing an organic-inorganic composite filler having,
      a structure in which inorganic primary particles having a surface covered with an organic resin phase and having an average particle size of 10 to 1000 nm are bonded to each other via the organic resin phase, and
      pores having a pore volume of 0.01 to 0.30 $cm^3/g$ as measured by mercury intrusion porosimetry, wherein the pore volume corresponds to the volume of pores with pore sizes in the range of 1 to 500 nm are formed in the organic resin phase, and (B) mixing the organic-inorganic composite filler, a polymerizable monomer and a polymerization initiator with each other.

2. The method according to claim 1, wherein step (A) comprises the steps:

(A1) immersing inorganic agglomerated particles, which comprise agglomerates of inorganic primary particles with an average particle size of 10 to 1,000 nm, in a polymerizable monomer solution containing 100 parts by mass of an organic solvent, 3 to 70 parts by mass of a polymerizable monomer, and an effective amount of a polymerization initiator;

(A2) removing the organic solvent from the inorganic agglomerated particles after the immersion; and (A3) polymerizing and curing the polymerizable monomer with which the inorganic agglomerated particles are impregnated.

3. The method according to claim 2, further comprising a step of granulating the inorganic aggregated particles by spray drying a slurry containing the inorganic primary particles having an average particle size of 10 to 1000 nm, before step (A1).

4. A method of manufacturing the organic-inorganic composite filler comprising the steps:

(A1) immersing inorganic agglomerated particles, which comprise agglomerates of inorganic primary particles with an average particle size of 10 to 1,000 nm, in the polymerizable monomer solution containing 100 parts by mass of the organic solvent, 3 to 70 parts by mass of the polymerizable monomer, and the effective amount of the polymerization initiator;

(A2) removing the organic solvent from the inorganic agglomerated particles after the immersion;

(A3) polymerizing and curing the polymerizable monomer with which the inorganic agglomerated particles are impregnated, wherein the organic-inorganic composite filler having, the structure in which inorganic primary particles having the surface covered with the organic resin phase and having the average particle size of 10 to 1000 nm are bonded to each other via the organic resin phase, and pores having the pore volume of 0.01 to 0.30 $cm^3/g$ as measured by mercury intrusion porosimetry, wherein the pore volume corresponds to the volume of pores with pore sizes in the range of 1 to 500 nm are formed in the organic resin phase.

* * * * *